(12) United States Patent
Josch et al.

(10) Patent No.: US 10,144,681 B2
(45) Date of Patent: *Dec. 4, 2018

(54) PROCESS FOR THE OXIDATIVE DEHYDROGENATION OF N-BUTENES TO BUTADIENE

(71) Applicant: BASF SE, Ludwigshafen (DE)

(72) Inventors: Jan Pablo Josch, Neustadt (DE); Alexander Weck, Freinsheim (DE); Sonja Giesa, Darmstadt (DE); Steffen Bütehorn, Mannheim (DE); Ragavendra Prasad Balegedde Ramachandran, Ludwigshafen (DE); Regina Benfer, Altrip (DE); Markus Weber, Limburgerhof (DE)

(73) Assignee: BASF SE (DE)

( * ) Notice: Subject to any disclaimer, the term of this patent is extended or adjusted under 35 U.S.C. 154(b) by 193 days.

This patent is subject to a terminal disclaimer.

(21) Appl. No.: 14/150,239

(22) Filed: Jan. 8, 2014

(65) Prior Publication Data

US 2014/0200379 A1    Jul. 17, 2014

Related U.S. Application Data

(60) Provisional application No. 61/752,530, filed on Jan. 15, 2013.

(51) Int. Cl.
*C07C 5/327* (2006.01)
*C07C 5/48* (2006.01)
*C07C 7/08* (2006.01)
*C07C 7/11* (2006.01)

(52) U.S. Cl.
CPC .................. *C07C 5/48* (2013.01); *C07C 7/08* (2013.01); *C07C 7/11* (2013.01)

(58) Field of Classification Search
CPC ....................................................... C07C 5/48
USPC ........... 585/326, 615, 616, 800; 95/263, 265
See application file for complete search history.

(56) References Cited

U.S. PATENT DOCUMENTS

| | | |
|---|---|---|
| 3,464,930 A | 9/1969 | Friedrichsen et al. |
| 3,536,775 A | 10/1970 | Hutson et al. |
| 3,799,886 A | 3/1974 | Felice et al. |
| 3,911,039 A | 10/1975 | Grasselli et al. |
| 3,932,551 A | 1/1976 | Grasselli et al. |

(Continued)

FOREIGN PATENT DOCUMENTS

| | | |
|---|---|---|
| DE | 734026 C | 4/1943 |
| DE | 1 642 921 A1 | 5/1971 |

(Continued)

OTHER PUBLICATIONS

"Guidelines for Safe Storage and Handling of Reactive Materials", Wiley: New York, 1995; p. 242.*

(Continued)

*Primary Examiner* — Philip Y Louie
*Assistant Examiner* — Aaron W Pierpont
(74) *Attorney, Agent, or Firm* — Drinker Biddle & Reath LLP

(57) ABSTRACT

A process for the oxidative dehydrogenation of n-butenes to butadiene is disclosed herein, in which the formation of butadiene peroxides from butadiene in the work-up of the product gas mixture from the oxidative dehydrogenation is effectively prevented.

6 Claims, 1 Drawing Sheet

(56) References Cited

U.S. PATENT DOCUMENTS

| | | | |
|---|---|---|---|
| 3,943,185 A * | 3/1976 | Tschopp | C07C 5/48 585/380 |
| 3,956,181 A | 5/1976 | Grasselli et al. | |
| 4,162,234 A | 7/1979 | Grasselli et al. | |
| 4,259,211 A | 3/1981 | Krabetz et al. | |
| 4,297,247 A | 10/1981 | Krabetz et al. | |
| 4,305,843 A | 12/1981 | Krabetz et al. | |
| 4,336,409 A | 6/1982 | Yamamoto et al. | |
| 4,397,771 A | 8/1983 | Grasselli et al. | |
| 4,423,281 A | 12/1983 | Yamamoto et al. | |
| 4,424,141 A | 1/1984 | Grasselli et al. | |
| 4,438,217 A | 3/1984 | Takata et al. | |
| 4,547,615 A | 10/1985 | Yamamoto | |
| 4,595,788 A * | 6/1986 | Yamamoto | C07C 5/48 585/621 |
| 5,677,261 A | 10/1997 | Tenten et al. | |
| 5,910,608 A | 6/1999 | Tenten et al. | |
| 5,989,412 A | 11/1999 | Okagami et al. | |
| 6,383,976 B1 | 5/2002 | Arnold et al. | |
| 7,417,173 B2 | 8/2008 | Crone et al. | |
| 2004/0019240 A1 | 1/2004 | Hibst et al. | |
| 2005/0096483 A1 | 5/2005 | Dieterle et al. | |
| 2006/0205978 A1 | 9/2006 | Yunoki et al. | |
| 2007/0167661 A1 * | 7/2007 | Johann | C07C 5/333 585/616 |
| 2008/0177105 A1 | 7/2008 | Raichle et al. | |
| 2009/0171117 A1 | 7/2009 | Arnold et al. | |
| 2011/0034330 A1 | 2/2011 | Czaja et al. | |
| 2011/0319698 A1 * | 12/2011 | Sohn | C10G 7/00 585/841 |
| 2012/0130137 A1 | 5/2012 | Orita et al. | |
| 2013/0281748 A1 | 10/2013 | Cha et al. | |
| 2014/0163288 A1 | 6/2014 | Ruttinger et al. | |
| 2014/0163289 A1 | 6/2014 | Grune et al. | |
| 2014/0163290 A1 | 6/2014 | Grune et al. | |
| 2014/0163291 A1 | 6/2014 | Grune et al. | |
| 2014/0163292 A1 | 6/2014 | Grune et al. | |
| 2014/0200380 A1 | 7/2014 | Josch et al. | |
| 2014/0200381 A1 | 7/2014 | Josch et al. | |

FOREIGN PATENT DOCUMENTS

| | | |
|---|---|---|
| DE | 2 106 796 A1 | 8/1972 |
| DE | 24 40 329 A1 | 3/1975 |
| DE | 24 47 825 A1 | 8/1975 |
| DE | 25 30 959 A1 | 2/1976 |
| DE | 26 00 128 A1 | 7/1976 |
| DE | 26 26 887 A1 | 12/1977 |
| DE | 29 09 670 A1 | 10/1980 |
| DE | 29 09 671 A1 | 10/1980 |
| DE | 44 42 346 A1 | 5/1996 |
| DE | 1 00 46 957 A1 | 4/2002 |
| DE | 10 2007 005 606 A1 | 4/2008 |
| DE | 10 2007 004 961 A1 | 7/2008 |
| EP | 0 714 700 A2 | 6/1996 |
| EP | 1 005 908 A2 | 6/2000 |
| EP | 1 382 383 A1 | 1/2004 |
| EP | 2 256 101 A2 | 12/2010 |
| GB | 581902 A | 10/1946 |
| JP | S60-58928 A | 4/1985 |
| JP | H01503062 A | 10/1989 |
| JP | 2011/001341 A | 1/2011 |
| JP | 2011/006381 A | 1/2011 |
| KR | 20100028702 A | 3/2010 |
| WO | WO-87/07259 A1 | 12/1987 |
| WO | WO-02/24620 A2 | 3/2002 |
| WO | WO-2005/047226 A1 | 5/2005 |
| WO | WO-2005/063658 A1 | 7/2005 |
| WO | WO-2006/050969 A1 | 5/2006 |
| WO | WO-2006/061202 A1 | 6/2006 |
| WO | WO-2006/091005 A1 | 8/2006 |
| WO | WO-2009/124945 A2 | 10/2009 |
| WO | WO-2010/137595 A1 | 12/2010 |
| WO | WO-2013/002459 A1 | 1/2013 |
| WO | WO-2013/136434 A1 | 9/2013 |

OTHER PUBLICATIONS

Reinhardt, H.-J.; Himmen; H.R. "Inerting in the Chemical industry"; Apr. 2010; pp. 1-15.*

Jung, J. C., et al., "Catalytic Performance of Bismuth Molybdate Catalysts in the Oxidative Dehydrogenation of $C_4$ Raffinate-3 to 1,3-Butadiene", Applied Catalysis A: General, 2007, vol. 317, pp. 244-249.

Jung, J. C., et al., "Production of 1,3-Butadiene From $C_4$ Raffinate-3 Through Oxidative Dehydrogenation of $n$-Butene Over Bismuth Molybdate Catalysts", Catal. Surv. Asia, 2009, vol. 13, pp. 78-93.

Alexander, D. S., "Explosions in Butadiene Systems", Industrial and Engineering Chemistry, 1959, vol. 51, No. 6, pp. 733-738.

Zabicky, J., "Analytical and Safety Aspects of Organic Peroxides and Related Functional Groups", in "PATAI's Chemistry of Functional Groups", John Wiley & Sons, Ltd., Chichester, UK, Dec. 2009.

English Translation of Japanese Office Action for Japanese Application No. 2015-553063, received Jun. 23, 2017.

* cited by examiner

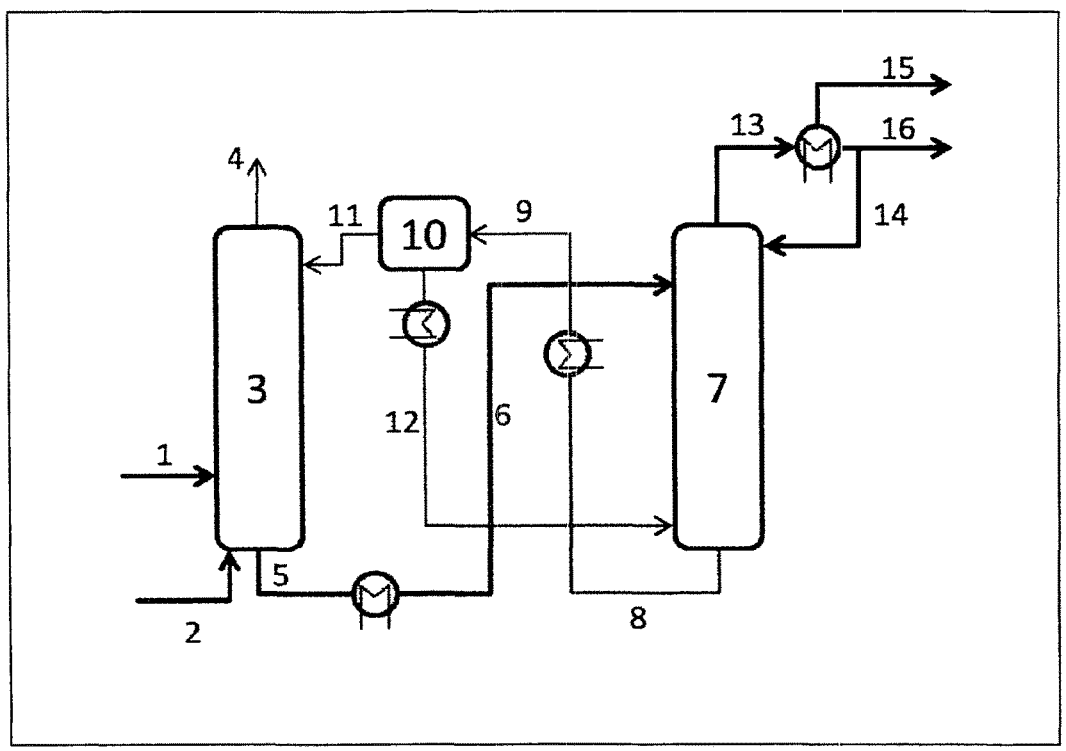

PROCESS FOR THE OXIDATIVE DEHYDROGENATION OF N-BUTENES TO BUTADIENE

CROSS-REFERENCE TO RELATED APPLICATIONS

This application claims benefit (under 35 USC 119(e)) of U.S. Provisional Application No. 61/752,530, filed Jan. 15, 2013, which is incorporated by reference.

FIELD OF THE INVENTION

The invention relates to a process for the oxidative dehydrogenation of n-butenes to butadiene.

BACKGROUND OF THE INVENTION

Butadiene is an important basic chemical and is used, for example, for preparing synthetic rubbers (butadiene homopolymers, styrene-butadiene rubber or nitrile rubber) or for preparing thermoplastic terpolymers (acrylonitrile-butadiene-styrene copolymers). Butadiene can also be converted into sulfolane, chloroprene and 1,4-hexamethylene-diamine (via 1,4-dichlorobutene and adiponitrile). Furthermore, vinylcyclohexene can be produced by dimerization of butadiene and can be dehydrogenated to styrene.

Butadiene can be prepared by thermal dissociation (steam cracking) of saturated hydrocarbons, with naphtha usually being used as raw material. In the steam cracking of naphtha, a hydrocarbon mixture of methane, ethane, ethene, acetylene, propane, propene, propyne, allene, butanes, butenes, butadiene, butynes, methylallene, $C_5$-hydrocarbons and higher hydrocarbons is obtained.

Butadiene can also be obtained by oxidative dehydrogenation of n-butenes (1-butene and/or 2-butene). Any desired mixture comprising n-butenes can be utilized as starting gas mixture for the oxidative dehydrogenation of the n-butenes to butadiene. For example, it is possible to use a fraction which comprises n-butenes (1-butene and/or 2-butene) as main constituent and has been obtained from the $C_4$ fraction from a naphtha cracker by removal of butadiene and isobutene. Furthermore, it is also possible to use gas mixtures which comprise 1-butene, cis-2-butene, trans-2-butene or mixtures thereof and have been obtained by dimerization of ethylene as starting gas. Gas mixtures which comprise n-butenes and have been obtained by fluid catalytic cracking (FCC) can also be used as starting gas.

Gas mixtures which comprise n-butenes and are used as starting gas in the oxidative dehydrogenation of n-butenes to butadiene can also be produced by nonoxidative dehydrogenation of n-butane-comprising gas mixtures. WO2005/063658 discloses a process for preparing butadiene from n-butane, which comprises the steps
a) provision of a feed gas stream a comprising n-butane;
b) introduction of the feed gas stream a comprising n-butane into at least one first dehydrogenation zone and nonoxidative catalytic dehydrogenation of n-butane, giving a product gas stream b comprising n-butane, 1-butene, 2-butene, butadiene, hydrogen, low-boiling secondary constituents and possibly water vapor;
c) introduction of the product gas stream b from the nonoxidative catalytic dehydrogenation and an oxygen-comprising gas into at least one second dehydrogenation zone and oxidative dehydrogenation of 1-butene and 2-butene, giving a product gas stream c which comprises n-butane, 2-butene, butadiene, hydrogen, low-boiling secondary constituents and water vapor and has a higher content of butadiene than the product gas stream b;
d) removal of hydrogen, the low-boiling secondary constituents and water vapor to give a $C_4$ product gas stream d which consists essentially of n-butane, 2-butene and butadiene;
e) separation of the $C_4$ product gas stream d into a recycle stream e1 consisting essentially of n-butane and 2-butene and a stream e2 consisting essentially of butadiene by extractive distillation and recirculation of the stream e1 to the first dehydrogenation zone.

This process has particularly effective utilization of the raw materials. Thus, losses of the raw material n-butane are minimized by recirculation of unreacted n-butane to the dehydrogenation. A high butadiene yield is achieved by the coupling of nonoxidative catalytic dehydrogenation and oxidative dehydrogenation. Compared to the production of butadiene by cracking, the process has a high selectivity. No coproducts are obtained. The complicated separation of butadiene from the product gas mixture from the cracking process is dispensed with.

The residual oxygen can be a problem since it can bring about butadiene peroxide formation in downstream process steps and can act as initiator for polymerization reactions. This risk exists particularly in regions in which butadiene is present in high concentrations and as pure material, since it is known that unstabilized 1,3-butadiene can form hazardous butadiene peroxides in the presence of oxygen. In the above-described process, this risk is present particularly in step e) in which butadiene is separated from the remaining C4-hydrocarbons. These risks are discussed, for example, by D. S. Alexander (Industrial and Engineering Chemistry 1959, 51, 733-738). These peroxides are viscous liquids. Their density is greater than that of butadiene. In addition, since they are only sparingly soluble in liquid 1,3-butadiene, they settle out on the bottom of storage vessels. Despite their relatively low chemical reactivity, the peroxides are very unstable compounds which can decompose spontaneously at temperatures in the range from 85 to 110° C. A particular hazard is the high shock sensitivity of the peroxides which explode with the brisance of an explosive. The risk of polymer formation is present, in particular, in the isolation of butadiene by distillation and can there lead to deposits of polymers (formation of "popcorn") in the columns.

WO2006/05969 describes a process for oxidative dehydrogenation in which removal of oxygen is carried out immediately after the oxidative dehydrogenation by means of a catalytic combustion step. In the catalytic combustion step, the oxygen is reacted with hydrogen added in this step in the presence of a catalyst.

This can reduce the oxygen content to small traces. Disadvantages of the catalytic combustion step are the consumption of hydrogen and also secondary reactions in which part of the 1,3-butadiene is burnt in the presence of oxygen and hydrogenated by hydrogen to form butene and butane.

BRIEF DESCRIPTION OF THE DRAWINGS

The FIGURE shows an embodiment of the process of the invention.

DETAILED DESCRIPTION OF THE INVENTION

It is an object of the invention to provide a process for the oxidative dehydrogenation of n-butenes to butadiene, in which the formation of butadiene peroxides from butadiene in the work-up of the product gas mixture from the oxidative dehydrogenation is effectively prevented.

The object is achieved by a process for preparing butadiene from n-butenes, which comprises the following steps:
A) provision of a feed gas stream a comprising n-butenes;
B) introduction of the feed gas stream a comprising n-butenes and an oxygen-comprising gas into at least one dehydrogenation zone and oxidative dehydrogenation of n-butenes to butadiene, giving a product gas stream b comprising butadiene, unreacted n-butenes, water vapor, oxygen, low-boiling hydrocarbons, possibly carbon oxides and possibly inert gases;
C) cooling and compression of the product gas stream b in at least one compression stage, giving at least one condensate stream c1 comprising water and a gas stream c2 comprising butadiene, n-butenes, water vapor, oxygen, low-boiling hydrocarbons, possibly carbon oxides and possibly inert gases;
D) separation of incondensable and low-boiling gas constituents comprising oxygen, low-boiling hydrocarbons, possibly carbon oxides and possibly inert gases as gas stream d2 from the gas stream c2 by
  Da) absorption of the $C_4$-hydrocarbons comprising butadiene and n-butenes in a high-boiling absorption medium, giving an absorption medium stream loaded with $C_4$-hydrocarbons and the gas stream d2,
  Db) removal of oxygen from the absorption medium stream loaded with $C_4$-hydrocarbons by stripping with an incondensable gas and
  Dc) desorption of the $C_4$-hydrocarbons from the loaded absorption medium stream to give a $C_4$-hydrocarbon stream d1 which comprises less than 100 ppm of oxygen;
E) separation of the $C_4$ product stream d1 by extractive distillation with a solvent which is selective for butadiene into a stream e1 comprising butadiene and the selective solvent and a stream e2 comprising n-butenes;
F) distillation of the stream e1 comprising butadiene and the selective solvent to give a stream f1 consisting essentially of the selective solvent and a butadiene-comprising stream f2.

In a step A), a feed gas stream a comprising n-butenes is provided.

As feed gas stream a, it is possible to use pure n-butenes (1-butene and/or cis-/trans-2-butene) and also gas mixtures comprising butenes. Such a gas mixture can be obtained, for example, by nonoxidative dehydrogenation of n-butane. It is also possible to use a fraction which comprises n-butenes (1-butene and cis-/trans-2-butene) as main constituent and has been obtained from the $C_4$ fraction from naphtha cracking by removal of butadiene and isobutene. Furthermore, it is also possible to use gas mixtures which comprise pure 1-butene, cis-2-butene, trans-2-butene or mixtures thereof and have been obtained by dimerization of ethylene as starting gas. Gas mixtures which comprise n-butenes and have been obtained by fluid catalytic cracking (FCC) can also be used as starting gas.

In an embodiment of the process of the invention, the starting gas mixture comprising n-butenes is obtained by nonoxidative dehydrogenation of n-butane. A high yield of butadiene, based on n-butane used, can be obtained by the coupling of a nonoxidative catalytic dehydrogenation with the oxidative dehydrogenation of the n-butenes formed. The nonoxidative catalytic dehydrogenation of n-butane gives a gas mixture which comprises butadiene, 1-butene, 2-butene and unreacted n-butane and also secondary constituents.

Usual secondary constituents are hydrogen, water vapor, nitrogen, CO and $CO_2$, methane, ethane, ethene, propane and propene. The composition of the gas mixture leaving the first dehydrogenation zone can vary greatly depending on the way in which the dehydrogenation is carried out. Thus, when the dehydrogenation is carried out with introduction of oxygen and additional hydrogen, the product gas mixture has a comparatively high content of water vapor and carbon oxides. In the case of modes of operation without introduction of oxygen, the product gas mixture from the nonoxidative dehydrogenation has a comparatively high content of hydrogen.

In step B), the feed gas stream a comprising n-butenes and an oxygen-comprising gas are fed into at least one dehydrogenation zone and the butenes comprised in the gas mixture are oxidatively dehydrogenated to butadiene in the presence of an oxydehydrogenation catalyst.

Catalysts suitable for the oxydehydrogenation are generally based on an Mo—Bi—O-comprising multimetal oxide system which generally additionally contains iron. In general, the catalyst system comprises further additional components such as potassium, cesium, magnesium, zirconium, chromium, nickel, cobalt, cadmium, tin, lead, germanium, lanthanum, manganese, tungsten, phosphorus, cerium, aluminum or silicon. Iron-comprising ferrites have also been proposed as catalysts.

In a preferred embodiment, the multimetal oxide comprises cobalt and/or nickel. In a further preferred embodiment, the multimetal oxide comprises chromium. In a further preferred embodiment, the multimetal oxide comprises manganese.

Examples of Mo—Bi—Fe—O-comprising multimetal oxides are Mo—Bi—Fe—Cr—O— or Mo—Bi—Fe—Zr—O-comprising multimetal oxides. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x+SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}Ni_{2.5}Mn_{0.5}K_{0.1}O_x$ and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$) DE-A 25 30 959 and DE-A 24 47 825 ($Mo_{12}BiFe_3Co_{4.5}Ni_{2.5}W_{0/5}K_{0.1}O_x$).

Suitable multimetal oxides and their preparation are also described in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x+SiO_2$) and DE-A 24 40 329 ($Mo_{12}BiCo_{4.5}Ni_{2.5}Cr_3P_{0.5}K_{0.1}O_x$).

Particularly preferred catalytically active multimetal oxides comprising molybdenum and at least one further metal have the general formula (Ia):

$$Mo_{12}Bi_aFe_bCo_cNi_dCr_eX^1_fX^2_gO_y \qquad (Ia),$$

where
$X^1$=Si, Mn and/or Al,
$X^2$=Li, Na, K, Cs and/or Rb,
$0.2 \leq a \leq 1$,
$0.5 \leq b \leq 10$,
$0 \leq c \leq 10$,
$0 \leq d \leq 10$,
$2 \leq c+d \leq 10$
$0 \leq e \leq 2$,
$0 \leq f \leq 10$
$0 \leq g \leq 0.5$, y=a number determined by the valence and abundance of the elements other than oxygen in (la) in order to maintain charge neutrality.

Preference is given to catalysts whose catalytically active oxide composition has only Co from among the two metals Co and Ni (d=0). $X^1$ is preferably Si and/or Mn and $X^2$ is preferably K, Na and/or Cs, with particular preference being given to $X^2$=K.

The gas comprising molecular oxygen generally comprises more than 10% by volume, preferably more than 15% by volume and even more preferably more than 20% by volume, of molecular oxygen. It is preferably air. The upper limit to the content of molecular oxygen is generally 50% by volume or less, preferably 30% by volume or less and even more preferably 25% by volume or less. In addition, the gas comprising molecular oxygen can further comprise any inert gases. Possible inert gases which may be mentioned are nitrogen, argon, neon, helium, CO, $CO_2$ and water. The amount of inert gases in the case of nitrogen is generally 90% by volume or less, preferably 85% by volume or less and even more preferably 80% by volume or less. In the case of constituents other than nitrogen, it is generally 10% by volume or less, preferably 1% by volume or less.

To carry out the oxidative dehydrogenation with complete conversion of n-butenes, preference is given to a gas mixture having a molar oxygen:n-butenes ratio of at least 0.5. Preference is given to working at an oxygen:n-butenes ratio of from 0.55 to 10. To adjust this value, the starting gas can be mixed with oxygen or an oxygen-comprising gas, for example air, and optionally additional inert gas or steam. The oxygen-comprising gas mixture obtained is then fed to the oxydehydrogenation.

The reaction temperature of the oxydehydrogenation is generally controlled by means of a heat transfer medium which is present around the reaction tubes. Possible liquid heat transfer media of this type are, for example, melts or salts such as potassium nitrate, potassium nitrite, sodium nitrite and/or sodium nitrate and also melts of metals such as sodium, mercury and alloys of various metals. However, ionic liquids or heat transfer oils can also be used. The temperature of the heat transfer medium is in the range from 220 to 490° C. and preferably in the range from 300 to 450° C. and particularly preferably in the range from 350 to 420° C.

Owing to the exothermic nature of the reactions which proceed, the temperature in particular sections of the interior of the reactor can be higher than that of the heat transfer medium during the reaction and a hot spot is formed. The position and magnitude of the hot spot is determined by the reaction conditions, but it can also be regulated via the dilution ratio of the catalyst bed or the flow of mixed gas through the bed. The difference between hot spot temperature and temperature of the heat transfer medium is generally 1-150° C., preferably 10-100° C. and particularly preferably 20-80° C. The temperature at the end of the catalyst bed is generally 0-100° C. above, preferably 0.1-50° C. above, particularly preferably 1-25° C. above, the temperature of the heat transfer medium.

The oxydehydrogenation can be carried out in all fixed-bed reactors known from the prior art, for example in a tray oven, in a fixed-bed tube reactor or shell-and-tube reactor or in a plate heat exchanger reactor. A shell-and-tube reactor is preferred.

The oxidative dehydrogenation is preferably carried out in fixed-bed tube reactors or fixed-bed shell-and-tube reactors. The reaction tubes are (like the other elements of the shell-and-tube reactor) generally made of steel. The wall thickness of the reaction tubes is typically from 1 to 3 mm. Their diameter is generally (uniformly) from 10 to 50 mm or from 15 to 40 mm, frequently from 20 to 30 mm. The number of reaction tubes accommodated in the shell-and-tube reactor is generally at least 1000, or 3000, or 5000, preferably at least 10 000. The number of reaction tubes accommodated in the shell-and-tube reactor is frequently from 15 000 to 30 000 or up to 40 000 or up to 50 000. The length of the reaction tubes is normally a few meters, with a reaction tube length in the range from 1 to 8 m, frequently from 2 to 7 m, often from 2.5 to 6 m, being typical.

Furthermore, the catalyst bed installed in the reactor can consist of a single zone or of two or more zones. The zones can consist of a pure catalyst or be diluted with a material which does not react with the starting gas or components of the product gas of the reaction. Furthermore, the catalyst zones can comprise all-active catalysts or supported coated catalysts.

The product gas stream leaving the oxidative dehydrogenation comprises not only butadiene but generally also unreacted 1-butene, 2-butene, oxygen and water vapor. It generally further comprises carbon monoxide, carbon dioxide, inert gases (mainly nitrogen), low-boiling hydrocarbons such as methane, ethane, ethene, propane and propene, butane and isobutane, possibly hydrogen and possibly oxygen-comprising hydrocarbons, known as oxygenates, as secondary constituents.

In step C), the product gas stream b is cooled and compressed in at least one compression stage, giving at least one condensate stream c1 comprising water and a gas stream c2 comprising butadiene, n-butenes, oxygen, water vapor, low-boiling hydrocarbons, possibly carbon oxides and possibly inert gases.

The product gas stream at the reactor outlet has a temperature close to the temperature at the end of the catalyst bed. The product gas stream is then brought to a temperature of 150-400° C., preferably 160-300° C., particularly preferably 170-250° C. It is possible to insulate the line through which the product gas stream flows in order to keep the temperature in the desired range, but use of a heat exchanger is preferred. This heat exchanger system can be any system as long as the temperature of the product gas can be kept at the desired level by means of this system. Examples of a heat exchanger are coil heat exchangers, plate heat exchangers, double-tube heat exchangers, multitube heat exchangers, boiler coil heat exchangers, boiler wall heat exchangers, liquid-liquid contact heat exchangers, air heat exchangers, direct contact heat exchangers and finned tube heat exchangers. Since part of the high-boiling by-products comprised in the product gas can precipitate while the temperature of the product gas is adjusted to the desired temperature, the heat exchanger system should therefore preferably have two or more heat exchangers. If two or more heat exchangers provided are arranged in parallel and distributed cooling of the product gas in the heat exchangers is made possible, the amount of high-boiling by-products which deposit in the heat exchangers decreases and the operating life of the heat exchangers can thus be increased. As an alternative to the abovementioned method, the two or more heat exchangers provided can be arranged in parallel. The product gas is fed to one or more, but not all, of the heat exchangers which after a particular period of operation are relieved by other heat exchangers. In this method, cooling can be continued, part of the heat of reaction can be recovered and, in parallel thereto, the high-boiling by-products deposited in one of the heat exchangers can be removed. As an organic solvent as mentioned above, it is possible to use any solvent without restriction as long as it is capable of dissolving the high-boiling by-products; as examples, it is possible to use an aromatic hydrocarbon solvent such as toluene, xylene, etc., or an alkaline aqueous solvent, e.g. an aqueous solution of sodium hydroxide.

A major part of the high-boiling secondary components and of the water can subsequently be separated off from the product gas stream b by cooling. This cooling and separation is preferably carried out in a quench. This quench can consist of one or more stages. Preference is given to a process in which the product gas stream b is brought into direct contact with the cooling medium and is cooled thereby. As cooling medium, preference is given to using water or an alkaline aqueous solution.

Preference is given to a two-stage quench. The cooling temperature for the product gas differs as a function of the temperature of the product gas obtained from the reactor outlet and of the cooling medium. In general, the product gas can, depending on the presence and temperature level of a heat exchanger, attain a temperature of 100-440° C., preferably 140-300° C., in particular 170-240° C., before the inlet to the quench. The product gas inlet into the quench has to be designed so that blocking by deposits at or immediately before the gas inlet is minimized or prevented. The product gas is brought into contact with the cooling medium in the 1st quenching stage. Here, the cooling medium can be introduced through a nozzle in order to achieve very efficient mixing with the product gas. For the same purpose, it is possible to install internals such as further nozzles through which the product gas and the cooling medium have to pass together in the quenching stage. The coolant inlet into the quench has to be designed so that blocking by deposits in the region of the coolant inlet is minimized or prevented.

In general, the product gas is cooled to 5-180° C., preferably to 30-130° C. and even more preferably to 60-90° C., in the first quenching stage. The temperature of the cooling medium at the inlet can generally be 25-200° C., preferably 40-120° C., in particular 50-90° C. The pressure in the first quenching stage is not subject to any particular restrictions but is generally 0.01-4 bar (gauge), preferably 0.1-2 bar (gauge) and particularly preferably 0.2-1 bar (gauge). When a large amount of high-boiling by-products is present in the product gas, polymerization among the high-boiling by-products or deposits of solid by-products caused by high-boiling by-products in this working step can easily occur. The cooling medium used in the cooling tower is frequently circulated, so that blockages due to solid precipitates can occur when the production of conjugated dienes is carried out continuously. The circulating flow of the cooling medium in liters per hour based on the mass flow of butadiene in grams per hour can generally be 0.0001-5 l/g, preferably 0.001-1 l/g and particularly preferably 0.002-0.2 l/g.

The dissolution of by-products of the ODH reaction, for example acetic acid, maleic anhydride, etc., in a cooling medium such as water occurs better at an elevated pH than at a low pH. Since the dissolution of by-products such as those mentioned above lowers the pH of, for example, water, the pH can be kept constant or increased by addition of an alkaline medium. In general, the pH at the bottom of the first quenching stage is kept in the range 2-14, preferably 3-13, particularly preferably 4-12. The more acidic the value, the less alkali medium has to be introduced. The more basic, the better does dissolution of some by-products occur. However, very high pH values lead to dissolution of by-products such as $CO_2$ and thus to a very high consumption of the alkaline medium. The temperature of the cooling medium at the bottom can generally be 27-210° C., preferably 45-130° C., in particular 55-95° C. Since the loading of the cooling medium with secondary components increases over the course of time, part of the loaded cooling medium can be taken off from the circuit and the circulating amount can be kept constant by addition of unloaded cooling medium. The ratio of amount discharged and amount added depends on the vapor loading of the product gas and the product gas temperature at the end of the first quenching stage. When the cooling medium is water, the amount added in the first quenching stage is generally lower than the amount discharged.

The cooled product gas stream which has been depleted in secondary components can then be fed to a second quenching stage. In this, it can again be brought into contact with a cooling medium.

In general, the product gas is cooled to from 5 to 100° C., preferably to 15-85° C. and even more preferably to 30-70° C., up to the gas outlet from the second quenching stage. The coolant can be introduced in countercurrent to the product gas. In this case, the temperature of the cooling medium at the coolant inlet can be 5-100° C., preferably 15-85° C., in particular 30-70° C. The pressure in the second quenching stage is not subject to any particular restrictions but is generally 0.01-4 bar (gauge), preferably 0.1-2 bar (gauge) and particularly preferably 0.2-1 bar (gauge). The cooling medium used in the cooling tower is frequently circulated so that blockages due to solid precipitates can occur when the preparation of conjugated dienes is carried out continuously. The circulating flow of the cooling medium in liters per hour based on the mass flow of butadiene in grams per hour can generally be 0.0001-5 l/g, preferably 0.001-1 l/g and particularly preferably 0.002-0.2 l/g.

The dissolution of by-products of the ODH reaction, for example acetic acid, maleic anhydride, etc., in a cooling medium such as water occurs better at an elevated pH than at a low pH. Since the dissolution of by-products such as those mentioned above lowers the pH of, for example, water, the pH can be kept constant or increased by addition of an alkaline medium. In general, the pH at the bottom of the second quenching stage is generally kept in the range 1-14, preferably in the range 2-12, particularly preferably in the range 3-11. The more acidic the value, the less alkaline medium has to be introduced. The more basic, the better does the dissolution of some by-products occur. However, very high pH values lead to dissolution of by-products such as $CO_2$ and thus to a very high consumption of the alkaline medium. The temperature of the cooling medium at the bottom can generally be 20-210° C., preferably 35-120° C., in particular 45-85° C. Since the loading of the cooling medium with secondary components increases over the course of time, part of the loaded cooling medium can be taken off from the circuit and the circulating amount can be kept constant by addition of unloaded cooling medium. The ratio of amount discharged to amount added depends on the vapor loading of the product gas and the product gas temperature at the end of the second quenching stage. When the cooling medium is water, the amount added in the second quenching stage is generally greater than the amount discharged.

To achieve very good contact of product gas and cooling medium, internals can be present in the second quenching stage. Such internals comprise, for example, bubble cap trays, centrifugal trays and/or sieve trays, columns having structured packings, e.g. sheet metal packings having a specific surface area of from 100 to 1000 m²/m³, e.g. Mellapak® 250 Y, and columns packed with random packing elements.

The circuits of the two quenching stages can either be separate from one another or be connected to one another. The desired temperature of the circulating streams can be set via suitable heat exchangers.

In order to minimize entrainment of liquid constituents from the quench into the offgas line, suitable constructional measures, for example the installation of a demister, can be undertaken. Furthermore, high-boiling substances which are not separated off from the product gas in the quench can be removed from the product gas by means of further constructional measures, for example gas scrubbers. A gas stream in which n-butane, 1-butene, 2-butenes, butadiene, possibly oxygen, hydrogen, water vapor, small amounts of methane, ethane, ethene, propane and propene, isobutane, carbon oxides and inert gases remain is obtained. Furthermore, traces of high-boiling components which are not separated off quantitatively in the quench can remain in this product gas stream.

Subsequently, in step C), the product gas stream b from the quench is compressed in at least one compression stage and then cooled further, with at least one condensate stream c1 comprising water condensing out and a gas stream c2 comprising butadiene, 1-butene, 2-butenes, oxygen, water vapor, possibly low-boiling hydrocarbons such as methane, ethane, ethene, propane and propene, butane and isobutane, possibly carbon oxides and possibly inert gases remaining.

The compression can be carried out in one or more stages. In general, compression is carried out overall from a pressure in the range from 1.0 to 4.0 bar (absolute) to a pressure in the range from 3.5 to 20 bar (absolute). Each compression stage is followed by a cooling stage in which the gas stream is cooled to a temperature in the range from 15 to 60° C. The condensate stream can thus also comprise a plurality of streams in the case of multistage compression. The condensate stream generally comprises at least 80% by weight, preferably at least 90% by weight, of water and additionally comprises small amounts of low-boilers, $C_4$-hydrocarbons, oxygenates and carbon oxides.

The gas stream c2 comprising butadiene, n-butenes, oxygen, low-boiling hydrocarbons (methane, ethane, ethene, propane, propene, n-butane, isobutane), possibly water vapor, possibly carbon oxides and possibly inert gases is fed as starting stream to the further work-up.

In a step D), incondensable and low-boiling gas constituents comprising oxygen, low-boiling hydrocarbons (methane, ethane, ethene, propane, propene), carbon oxides and inert gases are separated off as gas stream d2 from the gas stream c2 by absorption of the $C_4$-hydrocarbons in a high-boiling absorption medium and subsequent desorption of the $C_4$-hydrocarbons by Da) absorption of the $C_4$-hydrocarbons comprising butadiene and n-butenes in a high-boiling absorption medium, giving an absorption medium stream loaded with $C_4$-hydrocarbons and the gas stream d2, Db) removal of oxygen from the absorption medium stream loaded with $C_4$-hydrocarbons by stripping with an inert gas and Dc) desorption of the $C_4$-hydrocarbons from the loaded absorption medium stream, giving a $C_4$ product gas stream d1 which consists essentially of $C_4$-hydrocarbons and comprises less than 100 ppm of oxygen.

The $C_4$ product gas stream preferably comprises less than 50 ppm, particularly preferably less than 20 ppm and in particular less than 10 ppm, of oxygen.

For this purpose, the product gas stream c2 obtained after the water has been separated off is brought into contact with an inert absorption medium in the absorption stage Da) and the $C_4$-hydrocarbons are absorbed in the inert absorption medium, giving an absorption medium loaded with $C_4$-hydrocarbons and an offgas comprising the remaining gas constituents. In a desorption stage, the $C_4$-hydrocarbons are liberated again from the high-boiling absorption medium.

The absorption stage can be carried out in any suitable absorption column known to those skilled in the art. The absorption can be effected by simply passing the product gas stream through the absorption medium. However, it can also be carried out in columns or in rotational absorbers. It can be carried out in cocurrent, countercurrent or cross-current. The absorption is preferably carried out in countercurrent. Suitable absorption columns are, for example, tray columns having bubble cap trays, centrifugal trays and/or sieve trays, columns having structured packings, e.g. sheet metal packings having a specific surface area of from 100 to 1000 m²/m³, e.g. Mellapak® 250 Y, and columns packed with random packing elements. However, trickle towers and spray towers, graphite block absorbers, surface absorbers such as thick film and thin film absorbers and also rotational columns, plate scrubbers, crossed spray scrubbers and rotational scrubbers are also possible.

In one embodiment, the gas stream c2 comprising butadiene, n-butenes and the low-boiling and incondensable gas constituents is fed into the lower region of an absorption column. In the upper region of the absorption column, the high-boiling absorption medium is introduced.

Inert absorption media used in the absorption stage are generally high-boiling nonpolar solvents in which the $C_4$-hydrocarbon mixture to be separated off has a significantly greater solubility than do the remaining gas constituents to be separated off. Suitable absorption media are comparatively nonpolar organic solvents, for example aliphatic $C_8$-$C_{18}$-alkanes, or aromatic hydrocarbons such as middle oil fractions from paraffin distillation, toluene or ethers having bulky groups, or mixtures of these solvents, with a polar solvent such as 1,2-dimethyl phthalate being able to be added to these. Further suitable absorption media are esters of benzoic acid and of phthalic acid with straight-chain $C_1$-$C_8$-alkanols and also heat transfer oils such as biphenyl and diphenyl ether, chloro derivatives thereof and also triarylalkenes. One suitable absorption medium is a mixture of biphenyl and diphenyl ether, preferably having the azeotropic composition, for example the commercially available Diphyl®. This solvent mixture frequently comprises dimethyl phthalate in an amount of from 0.1 to 25% by weight.

Preferred absorption media are octanes, nonanes, decanes, undecanes, dodecanes, tridecanes, tetradecanes, pentadecanes, hexadecanes, heptadecanes and octadecanes or fractions which are obtained from refinery streams and comprise the abovementioned linear alkanes as main components.

In a preferred embodiment, an alkane mixture such as tetradecane (industrial C14-C17 fraction) is used as solvent for the absorption.

At the top of the absorption column, an offgas stream comprising essentially oxygen, low-boiling hydrocarbons (methane, ethane, ethene, propane, propene), possibly $C_4$-hydrocarbons (butane, butenes, butadiene), possibly inert gases, possibly carbon oxides and possibly water vapor is taken off. This stream can be partly fed to the ODH reactor. In this way, for example, the stream entering the ODH reactor can be adjusted to the desired $C_4$-hydrocarbon content.

At the bottom of the absorption column, residues of oxygen dissolved in the absorption medium are discharged by flushing with a gas in a further column. The remaining oxygen content should be so small that the stream d1 which leaves the desorption column and comprises butane, butene and butadiene comprises a maximum of 100 ppm of oxygen.

The stripping-out of the oxygen can be carried out in any suitable column known to those skilled in the art. Stripping can be effected by simply passing incondensable gases, preferably an inert gas such as nitrogen, through the loaded absorption solution. C4 also stripped out is washed back into the absorption solution by passing the gas stream through the absorption column. This can, in a preferred embodiment, be effected by direct installation of the stripper column below the absorber column. Since the pressure in the stripping column section and the absorption column section is, according to the invention, identical, this can be achieved by direct coupling. Suitable stripping columns are, for example, tray columns having bubble cap trays, centrifugal trays and/or sieve trays, columns having structured packings, e.g. sheet metal packings having a specific surface area of from 100 to 1000 $m^2/m^3$, e.g. Mellapak® 250 Y, and columns packed with random packing elements. However, trickle towers and spray towers and also rotational columns, plate scrubbers, crossed spray scrubbers and rotational scrubbers are also possible. Suitable gases are, for example, nitrogen or methane.

The absorption medium stream loaded with $C_4$-hydrocarbons is subsequently introduced into a desorption column. In a process variant, the desorption step Dc) is carried out by depressurization and/or heating of the loaded absorption medium. A preferred process variant is introduction of stripping steam and/or introduction of fresh steam into the bottom of the desorption column. The absorption medium which has been depleted in $C_4$-hydrocarbons can be fed as a mixture together with the condensed steam to a phase separation.

The absorption medium after stripping with steam preferably comprises from 70 to 100% by weight of high-boiling solvent and from 0 to 30% by weight of water, particularly preferably from 80 to 100% by weight of high-boiling solvent and from 0 to 20% by weight of water, in particular from 85 to 95% by weight of high-boiling solvent and from 5 to 15% by weight of water. The absorption medium which has been regenerated in the desorption stage is recirculated to the absorption stage.

The $C_4$ product gas stream d1 consisting essentially of n-butane, n-butenes and butadiene generally comprises from 20 to 80% by volume of butadiene, from 0 to 80% by volume of n-butane, from 0 to 10% by volume of 1-butene and from 0 to 50% by volume of 2-butenes, where the total amount is 100% by volume. Furthermore, small amounts of isobutane can be comprised.

The C4 product stream d1 is subsequently separated by extractive distillation using a solvent which is selective for butadiene into a stream e1 comprising butadiene and the selective solvent and a stream e2 comprising n-butenes.

The stream f2 consisting essentially of n-butane and 2-butene can be introduced in its entirety or partly into the $C_4$ feed to the ODH reactor. Since the butene isomers in this recycle stream consist essentially of 2-butenes and 2-butenes are generally oxidatively dehydrogenated more slowly to butadiene than 1-butene, this recycle stream can be catalytically isomerized before introduction into the ODH reactor. In this way, the isomer distribution can be brought to the isomer distribution present in thermodynamic equilibrium.

The extractive distillation can, for example, be carried out as described in "Erdöl and Kohle—Erdgas—Petrochemie", volume 34 (8), pages 343 to 346, or "Ullmanns Enzyklopädie der Technischen Chemie", volume 9, 4th edition 1975, pages 1 to 18. For this purpose, the $C_4$ product gas stream is brought into contact with an extractant, preferably an N-methylpyrrolidone (NMP)/water mixture, in an extraction zone. The extraction zone is generally configured in the form of a scrubbing column comprising trays, random packing elements or ordered packing as internals. It generally has from 30 to 70 theoretical plates in order to achieve sufficiently good separation performance. The scrubbing column preferably has a backwashing zone at the top of the column. This backwashing zone serves to recover the extractant comprised in the gas phase by means of a liquid hydrocarbon runback, for which purpose the overhead fraction is condensed beforehand. The mass ratio of extractant to $C_4$ product gas stream in the feed to the extraction zone is generally from 10:1 to 20:1. The extractive distillation is preferably operated at a temperature at the bottom in the range from 100 to 250° C., in particular at a temperature in the range from 110 to 210° C., a temperature at the top in the range from 10 to 100° C., in particular in the range from 20 to 70° C., and a pressure in the range from 1 to 15 bar, in particular in the range from 3 to 8 bar. The extractive distillation column preferably has from 5 to 70 theoretical plates.

Suitable extractants are butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, in particular N-methylpyrrolidone (NMP). In general, alkyl-substituted lower aliphatic acid amides or N-alkyl-substituted cyclic acid amides are used. Dimethylformamide, acetonitrile, furfural and in particular NMP are particularly advantageous.

However, it is also possible to use mixtures of these extractants with one another, e.g. NMP and acetonitrile, mixtures of these extractants with cosolvents and/or tert-butyl ethers, e.g. methyl tert-butyl ether, ethyl tert-butyl ether, propyl tert-butyl ether, n-butyl or isobutyl tert-butyl ether. NMP is particularly useful, preferably in aqueous solution, preferably with from 0 to 20% by weight of water, particularly preferably with from 7 to 10% by weight of water, in particular with 8.3% by weight of water.

The overhead product stream from the extractive distillation column comprises essentially butane and butenes and small amounts of butadiene and is taken off in gaseous or liquid form. In general, the stream consisting essentially of n-butane and 2-butene comprises from 50 to 100% by volume of n-butane, from 0 to 50% by volume of 2-butene and from 0 to 3% by volume of further constituents such as isobutane, isobutene, propane, propene and $C_5^+$-hydrocarbons.

In a step F), the stream e1 comprising butadiene and the selective solvent is separated by distillation into a stream f1 consisting essentially of the selective solvent and a stream f2 comprising butadiene.

The stream e1 obtained at the bottom of the extractive distillation column generally comprises the extractant, water, butadiene and small amounts of butenes and butane and is fed to a distillation column. In this, butadiene can be obtained at the top. At the bottom of the distillation column, a stream comprising extractant and possibly water is obtained, with the composition of the stream comprising extractant and water corresponding to the composition as introduced into the extraction. The stream comprising extractant and water is preferably recirculated to the extractive distillation.

In one variant, a side offtake stream comprising butadiene and the extractant is obtained in the distillation column and is transferred to a desorption zone. The desorption zone can, for example, be configured in the form of a scrubbing column having from 2 to 30, preferably from 5 to 20, theoretical plates and optionally a backwashing zone having, for example, 4 theoretical plates. This backwashing zone serves to recover the extractant comprised in the gas phase by means of a liquid hydrocarbon runback, for which purpose the overhead fraction composed of butadiene is condensed beforehand. Ordered packings, trays or random packing elements are provided as internals. The distillation is preferably carried out at a temperature at the bottom in the range from 100 to 300° C., in particular in the range from 150 to 200° C., and a temperature at the top in the range from 0 to 70° C., in particular in the range from 10 to 50° C. The pressure in the distillation column is preferably in the range from 1 to 10 bar. In general, a reduced pressure and/or an elevated temperature, compared to the extraction zone, prevail in the desorption zone.

The desired product stream obtained at the top of the column generally comprises from 90 to 100% by volume of butadiene, from 0 to 10% by volume of 2-butene and from 0 to 10% by volume of n-butane and isobutane. To purify the butadiene further, a further distillation according to the prior art can be carried out.

The invention is illustrated by the following examples.

Examples

An embodiment of the process of the invention is shown in the FIGURE. The reference numerals therein have the following meanings:

1: process gas stream comprising $O_2$, $N_2$, $C_4$-hydrocarbons, CO, $CO_2$, $H_2O$
2: stripping medium, incondensable gas
3: absorption and stripping column
5: absorption solution loaded with $C_4$-hydrocarbons, cooled
4: offgas stream comprising $O_2$, $N_2$, CO, $CO_2$
6: absorption solution loaded with $C_4$-hydrocarbons, heated
7: desorption column
8: unloaded absorption solution comprising $H_2O$
9: unloaded absorption solution comprising $H_2O$, cooled
10: phase separator
11: unloaded absorption solution
12: unloaded water
13: $C_4$-hydrocarbon stream, gaseous
14: $C_4$-hydrocarbon stream, liquid runback
15: gaseous $C_4$-hydrocarbon stream to the extractive distillation, still comprises inert gases
16: condensed $C_4$-hydrocarbon stream to the extractive distillation The process gas mixture leaving the compressor enters the absorption column as stream 1 having a temperature of 40° C. and the composition shown in table 1 at the 30th stage of the absorption column comprising 60 stages. The pressure at the top of the column is 10 bar absolute and the column has bubblecap trays.

TABLE 1

| Component | % by weight |
|---|---|
| BUTANE | 3.82 |
| ISO-BUTANE | 0.42 |
| ISO-BUTENE | 0.03 |
| 1-BUTENE | 0.01 |
| C-2-BUTENE | 0.35 |
| T-2-BUTENE | 1.04 |
| 1,3-BUTADIENE | 14.47 |
| $H_2O$ | 0.42 |
| TETRADECANE | 0.00 |
| $CO_2$ | 1.58 |
| $N_2$ | 70.44 |
| $O_2$ | 7.43 |

In the absorber column, the process gas stream 1 flows in countercurrent to the absorbent stream 11 comprising mainly tetradecane saturated with water which is introduced from the top. Here, the absorbent preferentially takes up the $C_4$-hydrocarbons and small proportions of the incondensable gases. The ratio of the mass of the absorbent stream 11 to the process gas stream 1 is 2.9:1. The lower part of the column is utilized as stripping column and nitrogen (stream 2) having a temperature of 35° C. is conveyed from the lowermost theoretical plate of the column in countercurrent to the loaded absorbent stream. The mass ratio of absorbent stream to nitrogen stream 2 is 98:1. As a result of this stripping, the oxygen is removed from the absorbent stream loaded with $C_4$ components and the stream 5 leaves the absorption column with a temperature of 46.6° C. and the composition shown in table 2.

TABLE 2

| Component | % by weight |
|---|---|
| BUTANE | 1.24 |
| ISO-BUTANE | 0.13 |
| ISO-BUTENE | 0.01 |
| 1-BUTENE | 0.00 |
| C-2-BUTENE | 0.11 |
| T-2-BUTENE | 0.34 |
| 1,3-BUTADIENE | 4.66 |
| $H_2O$ | 0.05 |
| TETRADECANE | 93.37 |
| $CO_2$ | 0.00 |
| $N_2$ | 0.08 |
| $O_2$ | 0.019 ppm |

The incondensable gases leave the absorption column mainly as stream 4 via the top of the column with a temperature of 35° C. and the composition shown in table 3.

TABLE 3

| Component | % by weight |
|---|---|
| BUTANE | 0.01 |
| ISO-BUTANE | 0.03 |
| ISO-BUTENE | 0.00 |
| 1-BUTENE | 0.00 |
| C-2-BUTENE | 0.00 |
| T-2-BUTENE | 0.00 |
| 1,3-BUTADIENE | 0.18 |
| $H_2O$ | 0.36 |
| TETRADECANE | 0.00 |
| $CO_2$ | 1.89 |
| $N_2$ | 88.53 |
| $O_2$ | 9.00 |

The absorption medium stream 5 is heated to 50° C. and enters the desorption column as stream 6 at the 30th plate of the desorption column comprising 36 bubblecap trays. The desorption column is operated at a pressure at the top of 5.5 bar absolute and in it the $C_4$-hydrocarbons are stripped out of the absorption mixture by means of the steam stream 12 having a temperature of 156° C. The mixture of water and absorption medium which is no longer loaded leaves the bottom of the desorption column as stream 8 with a temperature of 155° C. and has the composition shown in table 4.

TABLE 4

| Component | % by weight |
|---|---|
| BUTANE | 0.00 |
| ISO-BUTANE | 0.00 |
| ISO-BUTENE | 0.00 |
| 1-BUTENE | 0.00 |
| C-2-BUTENE | 0.00 |
| T-2-BUTENE | 0.00 |
| 1,3-BUTADIENE | 0.00 |
| $H_2O$ | 10.74 |
| TETRADECANE | 89.26 |
| $CO_2$ | 0.00 |
| $N_2$ | 0.00 |
| $O_2$ | 0.00 |

The stream 8 is subsequently cooled to 35° C., compressed to 10 bar absolute and separated in the decanter 10 into a tetradecane-rich stream 11 and an aqueous stream 12.

At the top of the desorption column, the $C_4$ components are taken off in stream 13 at a temperature of 48° C. and with the composition shown in table 5, subsequently cooled to 15° C. and thus partially condensed.

TABLE 5

| Component | % by weight |
|---|---|
| BUTANE | 18.86 |
| ISO-BUTANE | 1.93 |
| ISO-BUTENE | 0.13 |
| 1-BUTENE | 0.05 |
| C-2-BUTENE | 1.72 |
| T-2-BUTENE | 5.16 |
| 1,3-BUTADIENE | 70.80 |
| $H_2O$ | 0.67 |
| TETRADECANE | 0.00 |
| $CO_2$ | 0.04 |
| $N_2$ | 0.63 |
| $O_2$ | 0.00 |

The condensate is partly recirculated to the top of the desorption column. The mass ratio of the streams 14 and 15 is 1:1 here. The composition of the gaseous stream 15 and of the liquid stream 16 are shown in table 6.

TABLE 6

| Component | Stream 15 % by weight | Stream 16 % by weight |
|---|---|---|
| BUTANE | 9.92 | 18.99 |
| ISO-BUTANE | 1.54 | 1.94 |
| ISO-BUTENE | 0.07 | 0.13 |
| 1-BUTENE | 0.03 | 0.05 |
| C-2-BUTENE | 0.69 | 1.73 |
| T-2-BUTENE | 2.25 | 5.20 |
| 1,3-BUTADIENE | 38.66 | 71.26 |
| $H_2O$ | 0.15 | 0.68 |
| TETRADECANE | 0.00 | 0.00 |
| $CO_2$ | 2.36 | 0.01 |
| $N_2$ | 44.33 | 0.00 |
| $O_2$ | 10 ppm | 0.00 |

Under these operating conditions, an oxygen concentration of 10 ppm in the gas stream downstream of the $C_4$-absorption/desorption is achieved.

The invention claimed is:

1. A process for preparing butadiene from n-butenes, which comprises the following steps:
   A) providing a feed gas stream (a) comprising n-butenes;
   B) introducing the feed gas stream (a) comprising n-butenes and an oxygen-comprising gas into at least one dehydrogenation zone and oxidatively dehydrogenating the n-butenes to produce a product gas stream (b) comprising butadiene, n-butenes, water vapor, oxygen, low-boiling hydrocarbons selected from the group consisting of methane, ethane, ethene, propane, propene, butane, and isobutane;
   C) cooling and compressing the product gas stream (b) in at least one compression stage to produce both a gas stream (c2) and at least one condensate stream (c1) comprising water, wherein the gas stream (c2) comprises butadiene, n-butenes, water vapor, oxygen, low-boiling hydrocarbons selected from the group consisting of methane, ethane, ethene, propane, propene, butane, and isobutane;
   D) absorbing butadiene and n-butenes from the gas stream (c2) into an absorption medium comprising aromatic hydrocarbons in an absorption column to produce an absorption medium stream loaded with butadiene and n-butenes and a second gas stream (d2) comprising oxygen and low-boiling hydrocarbons selected from the group consisting of methane, ethane, ethene, propane, propene, butane, and isobutane;
   E) removing oxygen and a portion of butadiene and n-butenes from the absorption medium stream loaded with butadiene and n-butenes by stripping with an inert gas in a stripping column;
   F) recycling the portion of butadiene and n-butenes removed by said stripping into the absorption medium stream loaded with butadiene and n-butenes by passing the portion of butadiene and n-butenes removed by said stripping through the absorption column;
   G) desorbing the butadiene and n-butenes from the absorption medium stream loaded with butadiene and n-butenes to produce a $C_4$ product gas stream (d1) comprising the desorbed butadiene and n-butenes, wherein the $C_4$ product gas stream (d1) comprises less than 100 ppmw of oxygen;
   H) separating the $C_4$ product gas stream (d1) by extractive distillation with a solvent which is selective for butadiene into a stream (e1) comprising butadiene and the selective solvent and a stream (e2) comprising n-butenes; and
   I) distillation of distilling the stream (e1) comprising butadiene and the selective solvent to produce a stream (f1) consisting essentially of the selective solvent and a stream (f2) comprising butadiene.

2. The process according to claim 1, wherein the inert gas is nitrogen.

3. The process according to claim 1, wherein the C4 product gas stream (d1) comprises less than 20 ppmw of oxygen.

4. The process according to claim 1, wherein the inert gas is methane or nitrogen.

5. The process according to claim 4, wherein the inert gas is nitrogen.

6. The process according to claim 4, wherein the inert gas is methane.

* * * * *